United States Patent [19]

Bradley et al.

[11] Patent Number: 5,227,289
[45] Date of Patent: Jul. 13, 1993

[54] METHOD FOR IDENTIFYING MUTAGENIC AGENTS WHICH INDUCE LARGE, MULTILOCUS DELETIONS IN DNA

[76] Inventors: W. Edward C. Bradley, 3558 Marlowe, Montreal, Quebec, Canada, H4A 3L7; Abdelmajid Belouchi, 4598 Hampton, Montreal, Quebec, Canada, H4A 2L4; Pascale Dewyse, 6925 Bloomfield, Apt. #6, Montreal, Quebec, Canada, H3N 2G7

[21] Appl. No.: 524,551

[22] Filed: May 17, 1990

[51] Int. Cl.$^5$ .......................... C12G 1/68; C12G 1/02; C12N 15/00; C12N 5/00
[52] U.S. Cl. .......................................... 435/6; 435/29; 435/156; 435/172.1; 435/240.1; 935/10; 935/34
[58] Field of Search .................... 435/68, 6, 29, 156, 435/172.1

[56] References Cited

U.S. PATENT DOCUMENTS

| | | | |
|---|---|---|---|
| 4,066,510 | 1/1978 | Thylly | 435/6 |
| 4,302,535 | 11/1981 | Skopek et al. | 435/6 |
| 4,345,027 | 8/1982 | Dolbeare | 435/21 |
| 4,683,195 | 7/1987 | Mullis et al. | 435/6 |

OTHER PUBLICATIONS

Nalbantoglu et al N. Acid Res. 14(21):8361 (1986).
Diddens et al Int. J. Canc. 40:635 (1987).
Dewyse et al. Som. Cell & Mol. Gen. 16(3) 225 (1990).
Dewyse et al (1989) High Frequency Deletion Event at the aprt Locus of CHO Cells. Som. Cell & Mol Genet; 15(1) 19.
Bradley et al (1982) High Frequency Nonrandom Mutational Event at aprt Locus. Som. Cell Genet; 8(1) 51.
Subrata et al (1987) Specific Gene Amplification Associated with Consistent Chrom. Abnor CHO Chromosoma 95:117.
Simon A et al (1983) Mechanism of Mutation at the Aprt Locus in Chinese Hamster Ovary Cells.: Mol. and Cell Biol. 3(10) 1703.
Nalbantoglu et al. (1986) DNA Amplification-Delection in Spont Mutation of Hamster apr Locus. Nucleic Ac. Res. 14 (21) 8361.
Bradley et al. (1988) The aprt Heterozygote/-Hemizygote System for Screening Mutagenic Agents. Mut. Res. 199: 131.
Adir et al. (1980) Derivation of Chinese Hamster Ovary Cell Line He for Aprt & TK. Loc: Mut. Res. 72/187-205.

*Primary Examiner*—Robert A. Wax
*Assistant Examiner*—Miguel Escallon
*Attorney, Agent, or Firm*—Swabey Ogilvy Renault

[57] ABSTRACT

An assay is disclosed for identifying mutagenic agents which include large, multilocus deletion events in cultured mammalian cells. The cell lines used are adenine phosphoribosyltransferase heterozygotes derived from CHO cells, which we disclose possess a genomic sequence variation near the above-mentioned gene. We present the nucleotide sequence surrounding this variation, enabling an efficient determination of the proportion of deletion mutants among the mutant colonies induced by the agent to be tested.

2 Claims, 4 Drawing Sheets

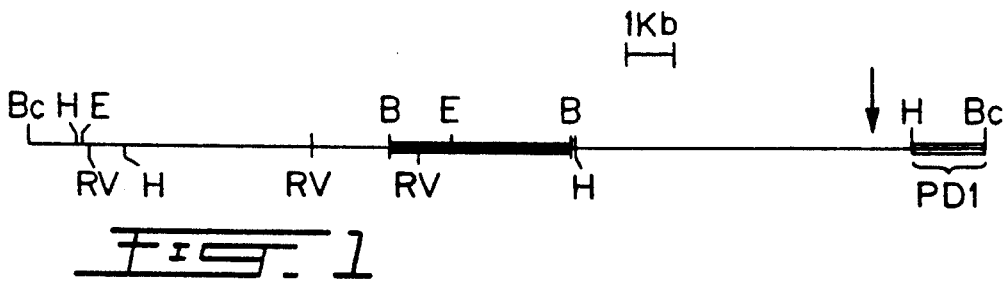

FIG. 1

```
         10         20         30         40         50         60
ACATCGGCTA TAAGTGCAAG TCGCTCTGGA GGGCTCCGAG CAGGAAGACG CCTAAGAAGG 70         80         90        100        110        120
CTGGAAATCA GGAAAGGCC- -AAGAAGGAC TGATTTCCTC ATCACCTGAT TTCCTCAGTC 130        140        150        160        170        180
ACTGCCACCC AACGCTCCCA GCACTCTGGA GGGAATGGCC ATGCACATAG TACTGTCATT 190        200        210        220        230        240
TTGGGCAAAG GTGGTCCCAA GGAGGAGGGC ATAAGGGGAG GGACAGCGCG GAAGCAGGAC 250        260        270        280        290        300
CTGGGAGACC TGGATAGCTG TAAGGACAAG CTGCACCGAA GGAGAGTTCC GAGGAGGTGG 310        320        330        340        350        360
GCGCTTGTAC AGTTCAGAGC ATCAATCTAA AATGCATCTG CAGGACCAGG ATTTAGTAGT
                                           PstI 370        380        390        400        410        420
GAGTTTCCAG ACTTGGTGCT CGCACCTCAT GGGTGTGGTA TGCCCTAGAG CCTCACAGCC 430        440        450        460        470        480
GGCGTGAGGT CTTCTGGATG CTTCGGAGCA ACCTTAGTAA CCATTCCACA TTAGTAAGGC   Primer#71

490        500        510        520        530        540
CACCCCTGGA AAGTAGGCCT TTGTATGACT CAGCATTGGA GCCCTCAGGA ATCTGTTTGC 550        560        570        580        590        600
CTCAGTGACA GGACAAAGCC AGCTGCCTGG TCACAGCTGA TAAGATAAGT GATGCATGGC
                                  BclI*

610        620        630        640        650        660
TGAGCCAATC AGATGTTTTC CTAGGACTAG AGAATGCTCT GGGGTAGGAA CTACCTCCAC 670        680        690        700        710        720
CCTGTGTGCT AGTGGCCTCT CAAGGTAAGG GCAAGCAAAA CAAGTGTAAC TCCAGAGGAC 730        740        750        760        770        780
TCAAGCCAGA CCCAGCAACT CAGGTGTTTT GAATAGATCC CTTGTTTGTT GTTGTTGTTC 790        800        810        820
GAGTGACGAG GATGACCAGC ATACACACAC AGCATCGACC TACATGAC
```

FIG. 4A

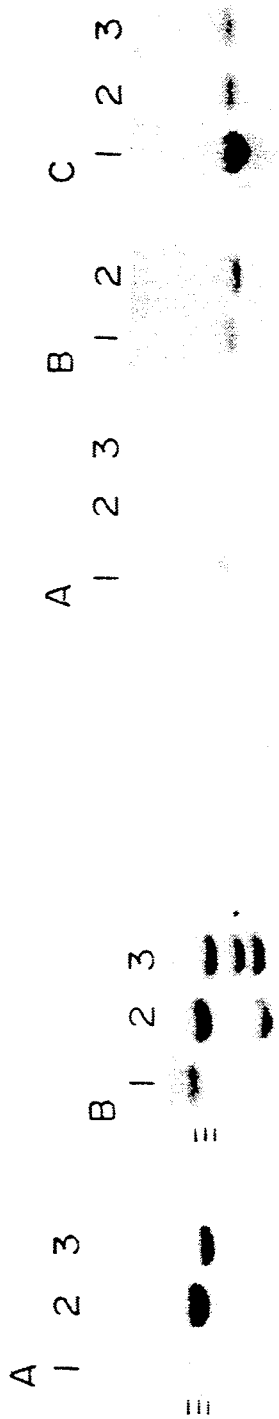

```
         10         20         30         40         50         60
    AGCAGACCXT AGTGAAGCTG TGTGTGTGTC GAGTATGAGA TGACCAGCAT ACACACACAA 70         80         90        100        110        120
    CGATGCACTA CATCTGACTG TGTGCTAACT GTGATAGTAT CTCTCATCAG CTCXGGGATT 130        140        150        160        170        180
    AGAGTCACAT GAAGGATTCC TCTCTCTTCC TTTCTTTCTT ATTTATTTTG AGTCAGGTTC 190        200        210        220        230        240
    TCTGTATATG AGTACTGGGC TGTCCTGGAA CTTGCTCTGT AGGCCAAACA CAGAGATCTG 250        260        270        280        290        300
    CCTGCTTCAC ACTCTGGCCA GGCCAGGCCC TCCCCCAAAC TGGGAAGCAA AACAACTCCT 310        320        330        340        350        360
    TACATTTTAT CAGATTTTTT GTCAAGGCCT CTTCCAATCC ATGGAACCTT AATTAAAACA 370        380        390        400        410        420
    TGGTCACAAA AAATCAAAGT AGCCTGGCAG TGGTGGACTG CTTATCCAGG CAGAGGCAGG 430        440        450        460        470        480
    CAGATCTCTG TGAGTTCAAG GCCAGCCTGG TCTACAAGGC AAGTTCCAGA CATCAGGCTA 490        500        510        520        530        540
    TTACACAGAG AAACTGTCTA AAAAAAAAGC CAAGCCAAAC CAAACCAAAC CAACAAACAA 550        560          7         17         27         37
    AAAAGCCACT CCACAGGAAG CTT
                           ─────
                           HindIII                    ◄──[Primer #53 (nucl.404 to 380)]
```

*FIG. 4B*

MARKER

BcII-DIGESTED

UNDIGESTED

MARKER

MARKER
12
11
10
9
8
7
6
5
4
3
2
1
MARKER

METHOD FOR IDENTIFYING MUTAGENIC AGENTS WHICH INDUCE LARGE, MULTILOCUS DELETIONS IN DNA

BACKGROUND OF THE INVENTION

There presently exists about 75,000 synthetic chemicals in commercial use, with the number increasing annually by about 1,000. All of these chemicals must be shown to be non-toxic or of limited toxicity before being introduced into the environment. In addition waste materials of advanced societies are accumulating at an exponential rate, all of which must be either deposed in land fill or some equivalent storage site, or treated to reduce their bulk or toxicity, and then released into the environment. As is the case with new synthetic chemicals, the toxic potential of all waste materials, either before or after treatment, must be known to permit responsible and ecologically sound management practices. The need for reliable means for testing toxicity is therefore great, and this need has been recognized for many years.

The procedure for genotoxicity testing is well established, and involves, generally speaking, a series of tests at increasing levels of complexity and expense: in vitro mutational assays on bacteria, mutation and/or transformation assays on cultured mammalian cells and then a variety of in vivo tests in animals, both short and long term. The choice of the battery of in vitro tests is important, as false negative results at this stage result in substantial expenses in time and money in undertaking the more elaborate animal studies. In these in vitro tests, bacterial or mammalian cells which carry a single functional copy of a given gene in their genetic make-up are treated with a suspected mutagen that some of the cells in the population may become mutant in this gene. This mutation changes the sequence of base pairs in the gene or biochemical deficiency within the cell. This cell is then selected for by growth in a medium containing an agent lethal for wild type cells, but innocuous to cells with the said deficiency. The number of mutant cell colonies obtained per million cells plated in the selective medium reflects the mutagenic activity. These producers are presented in detail in U.S. Pat. Nos. 4,066,510 and 4,302,535 issued to W. G. Thilly and T. R. Skepek et al, respectively.

One shortcoming of many of the cell strains in use is that the genetic locus carrying the gene to be assayed is hemizygous; that is the genetic sequences surrounding the aforesaid gene are present in only one copy per cell. For example, in the CHO/HGPRT assay developed specifically for genotoxicity testing, the hypoxanthine guanine phosphoribosyltransferase (HGPRT) gene is on the X-chromosome, which is present in only one copy in CHO cells. If a genotoxic agent induces large genetic deletions removing many genes including HGPRT (these deletions are referred to as multilocus events), a neighbouring gene whose protein product may be essential to the growth of the cell will also be removed and this will kill the cell.

A limited number of assay systems have been developed to overcome this shortcoming, Two cell lines, the mouse lymphocyte L5178Y line and the human lymphocyte TK6 line are presumed to be heterozygous at the thymidine kinase (TK) locus; that is, one of the two functional copies of the TK gene present in the parental cell has already been made non-functional by a small mutational event affecting the TK gene and no neighbouring genes. Mutant events occurring at the remaining normal locus may remove neighbouring sequences including any essential genes present, but even so a second, functional copy of each of these genes remains associated with the other copy of the TK gene which had previously been mutated. The cells made mutant at the second TK gene can therefore grow even if the mutation is a multilocus event.

An alternative cell line, called AS52, has been developed in which a single copy of a gene derived from bacteria, xanthine guanine phosphoribosyltransferase (gpt) was artificially introduced into the genome of a mammalian cell. The region of insertion is present in two copies in this cell line. These cells can be treated with a suspected mutagen, and any events which inactivate or remove the gpt gene can be detected by growing the treated cells in the appropriate selective medium, and multilocus events will not kill the cells because a second copy of each of the neighbouring genes remains in the cell.

A fourth cell line, D423, has been proposed as having the potential of overcoming the deficiencies of hemizygous cell lines. This is a so-called class III heterozygote, partially deficient in the level of functional adenine phosphoribosyltransferase (APRT). In a fashion similar to the above-mentioned $TK^{+/-}$ heterozygous lines, this line undergoes mutation to resistance to the drug 2,6 diaminopurine, and agents which induce multilocus deletions can induce mutations at the functional APRT gene without killing the cell. It is not clear how closely mutation in this cell reflects the process of mutation in normal cells, however, since 1) one of the chromosomes carrying APRT has been rearranged in D423 and 2) previous molecular analysis suggested there may be three copies of the APRT gene in this line.

An important part of the protocol in measuring mutation induced by a suspected mutagen is to perform the control experiment. A portion of the same population cells used for mutagen treatment is grown in the selective medium without such a treatment, in order to determine the number of mutants pre-existing in the population. This is called the spontaneous mutant frequency and it depends mostly on the probability that a given cell will undergo spontaneous mutation at the locus in question during a given cell cycle. This in turn is called the spontaneous mutation rate, and can be measured by the Luria-Delbruck fluctuation test. The sensitivity of a given mutagen assay depends directly on the level of the background of spontaneous mutants in the population, since a mutagenic effect cannot be detected unless the number of mutant colonies determined after treatment is higher than this background by a statistically significant amount.

One shortcoming of some of the heterozygous mammalian cell lines in use (including AS52) is that the spontaneous frequencies of mutation are high: the line L5178Y is variously reported to have spontaneous TK mutants at $3.5 \times 10^{-5}$ to $4 \times 10^{-4}$/cell; AS52 cultures have gpt mutants at between $3 \times 10^{-5}$ and $10^{-4}$/cell. TK6 cells are reportedly more stable, with spontaneous TK mutant frequencies at between 1 and $4 \times 10^{-6}$. This is achieved artificially, by first growing cells in a selective medium which kills mutant TK cells. The D423 line has a spontaneous mutation rate at the APRT locus at $3 \times 10^{-7}$, as measured by the Luria-Delbruck assay; two other class III APRT heterozygotes, D424 and D425, also have rates $<5 \times 10^{-7}$/cell/generation. Cultures of these cell lines usually have background incidences of mutants of <10$^{-6}$. Thus D423, D424 and D425 are particularly well suited to genotoxicity testing in this respect.

A refinement of the above-described procedure to determine genotoxicity of various agents consists of analysis of the nucleotide sequences of mutant cells to determine the nature of the mutational event. For example, to distinguish between point (small) mutations and multilocus events, an analysis of whether one or both copies of the mutated gene are still present in the cell can be made. This is possible if a known polymorphism exists which distinguishes the two sequences coding the for two copies of the gene being analysed. Such a polymorphism was reported near the TK gene in the cell line TK6, but its existence has not been confirmed by molecular analysis.

SUMMARY OF THE INVENTION

We present a cell line which, while having the advantage of being heterozygous at the APRT locus, is particularly well suited to overcoming the above-mentioned shortcomings of other heterozygous cell lines used to measure genotoxicity. Specifically its spontaneous mutation rate is $4.7 \times 10^{-7}$/cell/ generation, and mutant frequencies among recently cloned populations are usually <10$^{-6}$. We further present a variation (or polymorphism) close to the APRT locus which we demonstrate will permit analysis of the mutational spectrum (deletion vs point mutation) of both spontaneous and induced mutants. We further disclose the isolation and identification of the CHO genomic nucleotide sequence which carries the variation, and we present nucleotide sequence information allowing a rapid analysis of loss of this polymorphism in the mutants isolated from the heterozygous cell line.

BRIEF DESCRIPTION OF THE FIGURES

FIG. 1 is a representation of the genomic DNA sequence surrounding the APRT gene of the CHO cell line, showing the sequence variation we disclose herein (arrow).

FIG. 2 is a representation of a Southern blot of DNA from CHO cells digested from various enzymes.

FIG. 3 is a representation of a Southern blot of DNA from various cell lines derived from CHO cells, digested with BclI.

FIGS. 4a-4 is the partial nucleotide sequence of the genomic DNA surrounding the BclI variation.

DETAILED DESCRIPTION OF THE INVENTION

Figure 5:
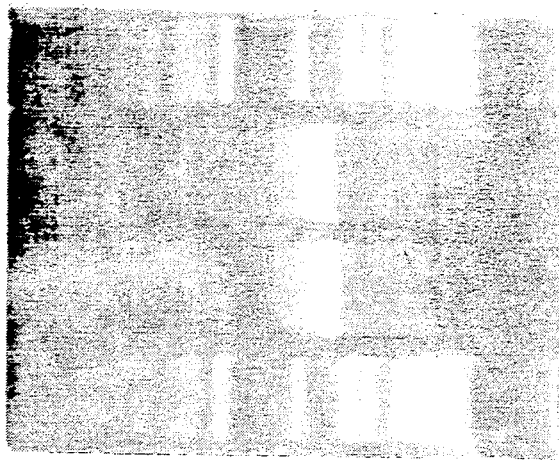
FIG. 5 shows an experiment wherein the DNA sequence of the hemizygous line D428 carrying the site of the BclI variation is amplified and digested by BclI, the digestion products being subsequently separated by agarose gel electrophoresis.

The test system of this invention, as exemplified herein, involves the isolation of a cell line which is heterozygous at the adenine phosphoribosyltransferase locus, and which undergoes mutation at the remaining functional copy of this gene, at a low and predictable spontaneous rate. The test system uses cells derived from the CHO cell line, which we disclose here has a sequence variation in the flanking region of the APRT gene, on the 3' side of this gene.

Referring now to FIG. 1, the genomic fragment of about 20 kilobases (kb) illustrated in this figure, which carries the APRT gene, was cloned in the vector λEMBL3, as described by Dewyse and Bradley, Somatic Cell Molec. Genet. 15, 19–28, 1989.

A physical map of the region surrounding the sequence variation was made by subcloning the 6 kb Hind III - HindIII fragment containing the variation which cannot be digested by BclI and into the plasmid pGEM-1 and digesting with various combinations of restriction endonucleases. A region from 340 bp to the left of the PstI site to the right hand HindIII site was partially sequenced, said sequences being presented in FIG. 4. The suspected cryptic BclI site is underlined.

In carrying out the invention, a CHO APRT class III heterozygote is treated with a suspected mutagen at various concentrations, sufficient to induce cell death at an incidence of 20–90%. After growth in non-selective medium for a sufficiently long period to permit expression of the APRT phenotype (4–5 days), the cells were removed from the culture dish, and a known number is placed in another dish or dishes with medium containing 30μg/ml 2,6 diaminopurine (DAP). After seven days the colonies are counted and the number compared with the number in control cultures that is those which were treated identically except that they were not exposed to the suspected mutagen. The colonies are removed from the culture dishes, and the mutant cells grown to a number large enough to permit molecular analysis. The DNA is then extracted from each mutant and analysed to determine whether one or both of the versions of the sequence variation is present. This can be done by either digesting the DNA with the enzyme BclI followed by Southern blot analysis in a manner described for FIG. 2, or in a more rapid way, by using the sequence information disclosed in FIG. 4, as follows: Oligodeoxynucleotide primers, provided as part of a kit and corresponding to the nucleotides indicated in FIG. 4 are added to 1 μg of DNA, along with buffers and the enzyme Taq polymerase (as described in U.S. Pat. No. 4683195 issued to Kary B. Mullis et al.). Following an appropriate number of temperature cycles the amplified DNA is extracted, digested with BclI and subjected to agarose gel electrophoresis. The presence of bands of 1.3 kb and 113 bp signifies that the allele carrying the functional BclI site was present; the presence of a band at 1.4 kb signifies that the other allele carrying the cryptic BclI site was present. It is therefore possible to quickly and directly assess what proportion of mutants in the induced culture vs in the control culture were deletions which removed the 3' flanking sequences of the APRT gene. This information is then statistically analysed to aid in determining whether there was an affect of the suspected mutagen, and whether said affect was to induce deletions.

EXAMPLE 1

Detection of a restriction fragment length variation near the APRT gene of CHO cells The clone λPD1, containing the wild type APRT allele and flanking sequences was analysed in further detail and the map presented was the result of this study (FIG. 1). However, as previously described by Dewyse and Bradley, Somatic Cell Molec. Genet. 15: 19–28, 1989, hybridization of the sequences the most downstream of APRT (probe PD1, FIG. 1) to DNA from λPD2 (which carried the MspI mutated APRT allele and flanking sequences from D416 cloned in λEMBL3) gave no signal which indicated the absence of this HindIII-BclI fragment in this clone. At the time, this was attributed this to an inherent instability of this sequence. Recently though, was used this fragment to probe a BclI digest of D416 and wild-type CHO and unexpectedly two bands were detected, the previously identified 19 kb fragment and an additional one of 2 kb.

Since the CHO line was established from an outbred animal, an explanation for these results is the existence of a BclI restriction fragment length variation (RFLV) which had so far gone unnoticed because of limited resolution in the separation of fragments within the size range of 17–20 kb. To test this, a combination of enzymes was employed which reduced the size of the detected fragments. BclI, EcoRI and BclI-EcoRI DNA digests of CHO DNA were hybridized consecutively with PD1 (FIG. 2A) and the APRT gene (3.9 kb BamHI fragment of pHaprt shown in FIG. 1 as the thick black line) (FIG. 2B). A 19 kb BclI fragment (lanes 1), 12.5 kb EcoRI fragment (lanes 2) and 10.5 kb BclI-EcoRI fragment (lanes 3) are recognised by both probes as predicted by the map (FIG. 1). The additional 2 kb BclI fragment detected by the PD1 probe (FIG. 2A, lane 1) and the 8.5 kb BclI-EcoRI fragment which hybridizes to APRT (FIG. 2B, lane 3) confirm the localisation of a second BclI site 2 kb upstream of the one previously mapped. Thus the established map is correct for both alleles with the exception of a newly discovered BclI site at one allele.

EXAMPLE 2

Detection of spontaneous deletion mutants at the APRT locus of CHO cells

Confirmation that the two BclI bands of 19 and 2 kb represent a RFLV was obtained by demonstrating loss of one allele in the deletion mutants derived from the heterozygote D416. These cells are known to be deletion mutants, having lost the functional copy of APRT in its entirety. DNA from two of these mutants (D416D'39 and D416D'48) was digested with BclI and probed with the HindIII-BclI fragment. As shown in FIG. 3A, the mutants retained the 2 kg fragment but had lost the 19 kb band (lanes 2,3). This is consistent with the deletion of one APRT allele and flanking sequences in the two sequences.

EXAMPLE 3

Use of the polymerase chain reaction to determine the genotype of a cell line, hemizygous at the APRT locus The oligodeoxynucleotides 5'GTAACCATT-CCACATTAGTAAGGCC3' and 5'TGGCAACT-CTAATGATCCTCAGGTG3' (nucleotides 404 to 380 in FIG. 7, Dewyse and Bradley, Somatic Cell Molec. Genet. 15, 19–28, 1989) are synthesized and prepared for use following the instructions of the manufacturer of the oligodeoxynucleotide synthesizer, Dupont Inc. These were then used as described above to amplify the 1.4 kb genomic DNA sequence of a class I hemizygote (D428), whose boundaries are defined by the said oligonucleotides. The DNA was purified by phenol extraction and one half was digested with the enzyme BclI. Both portions were subjected to agarose gel electrophoresis. FIG. 5 shows that the digested sample yielded bands only at 1.3 kb and 113 bp, compared with the undigested sample at 1.4 kb, thus showing that the only allele present in the line D428 is that carrying the intact BclI site.

EXAMPLE 4

Detection of deletions at the APRT locus of class III APRT heterozygotes

Figure 6:
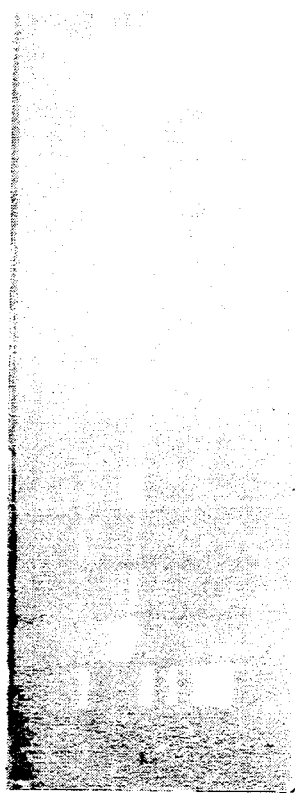
FIG. 6 shows an experiment where the same sequence is shown in FIG. 5 is amplified from a variety of cell lines and mutants.

Mutants of the cell lines D424 and D425 were isolated in 30 μg/ml DAP, as described, after treatment with ultraviolet (U.V.) or X-irradiation. DNA was extracted and amplified as described in Example 3. Each amplified sample was digested with the enzyme BclI and the reaction products separated on an agarose gel. FIG. 6 shows that the D425 (lane 12) line had both alleles, since bands at 1.4 and 1.3 kb were present (the digestion product of 113 bp is not visible on this gel). D428 (lane 11) yields only the 1.3 kb band. U.V.-induced mutants of either D424 (lands 1–3) or D425 (land 4) showed retention of both alleles (lanes 1–3) and in the one mutant derived from D425, loss of the allele associated with the normal gene. (U.V.-irradiation is generally thought to induce point mutations, but occasional large deletions have been reported). X-ray induced mutants, whose DNA is in lanes 5 and 6 (D424-derived) and 7–10 (D425-derived) all show loss of the 1.3 kb band, indicating a large deletion was responsible for the mutation. The CHO cell lines D424 and D425 and the probe PD1 are maintained in laboratories on Institut du Cancer de Montreal, in Montreal, Canada, and samples of the cell lines and probe are available on request.

Having described the invention as above, it will become evident to those having ordinary skill that many equivalents to the above embodiments of the invention are possible and such may be made without departing from the invention.

REFERENCE

P. Dewyse and W. E. C. Bradley (1989) Somatic Cell Molec. Genet. 15: 19–28.

We claim:

1. A method of identifying a mutagenic agent which includes a large, multilocus deletions in DNA in mammalian cells comprising:
   i) exposing a class III heterozygous CHO cell line to a potential mutagenic agent under investigation, and allowing any mutation of of cell line to proceed, said cell line being characterized in that a restriction fragment length variation exists in on mutation it becomes resistant to 2,6-diaminopurine and in that the DNA sequence adjacent the two alleles of the APRT gene such that the DNA sequence adjacent one of the two alleles can be digested with the enzyme BclI but the DNA sequence variation adjacent the other of the two alleles can not be digested with BclI,
   ii) isolating induced mutations of the cell line deficient in APRT function,
   iii) isolating DNA from the induced mutants,
   iv) digesting the isolated DNA with BclI enzyme to produce digested fragments including a 19 kb fragment and any 2 kb fragment, which fragments hybridize with the labeled probe derived from DNA fragment PD1,
   v) separating any digested fragments,
   vi) transferring the separated fragments of v) to a solid support, vii) hybridizing the supported separated fragments with a labeled probe derived from the clone DNA fragment PD1, viii) determining fragments having undergone loss of the 2 kb band identified by the probe, as an identification of parent mutants in which the loss occurred, and ix) evaluating the mutating ability of the potential mutagenic agent.

2. A method of identifying a mutagenic agent which induces large, multilocus deletions in DNA in mammalian cells comprising:

i) exposing a class III heterozygous CHO cell line to a potential mutagenic agent under investigation, and allowing any mutation of of cell line to proceed, said cell line being characterized in that a restriction fragment length variation exists in on mutation it becomes resistant to 2,6-diaminopurine and in that the DNA sequence adjacent the two alleles of the APRT gene such that the DNA sequence adjacent one of the two alleles can be digested with the enzyme BclI but the DNA sequence variation adjacent the other of the two alleles can not be digested with BclI, ii) isolating induced mutations of the cell line deficient in APRT function, iii) isolating DNA from the induced mutants, iv) amplifying the 1.4 kb region of the isolated DNA from iii) with the oligodeoxynucleotides 5'GTAACCATTCCACATTAGTAAGGCC3' and 5"TGGCAACTCTAATGATCCT-CAGGTG3', by polymerase chain reaction, v) digesting the amplified products of iv) with the restriction endonuclease BclI, analyzing the digestion products by agarose gel electrophoresis for fragments of 1.4 and 1.3 kb, said fragments being derived from DNA adjacent to the different alleles of said class III heterozygous CHO cell line, and viii) evaluating the mutating ability of the potential mutagenic agent.

* * * * *